United States Patent
Aoki et al.

(10) Patent No.: US 6,710,213 B2
(45) Date of Patent: Mar. 23, 2004

(54) PRODUCTION PROCESS AND USE FOR PROPARGYL ALCOHOL AND ITS INTERMEDIATE

(75) Inventors: Takanori Aoki, Kawasaki (JP); Takami Ohe, Kawasaki (JP); Haruki Ishikami, Kawasaki (JP); Makoto Saito, Kawasaki (JP); Toshitaka Hiro, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 112 days.

(21) Appl. No.: 09/822,488

(22) Filed: Apr. 2, 2001

(65) Prior Publication Data

US 2002/0010377 A1 Jan. 24, 2002

Related U.S. Application Data

(60) Provisional application No. 60/230,717, filed on Sep. 7, 2000, and provisional application No. 60/216,521, filed on Jul. 6, 2000.

(30) Foreign Application Priority Data

| Mar. 31, 2000 | (JP) | ................ | 2000-098454 |
| Jun. 5, 2000 | (JP) | ................ | 2000-167604 |
| Mar. 19, 2001 | (JP) | ................ | 2001-077641 |
| Mar. 19, 2001 | (JP) | ................ | 2001-077642 |

(51) Int. Cl.$^7$ .......................... C07C 33/04; C07C 31/18
(52) U.S. Cl. ............................. 568/873; 568/855
(58) Field of Search .......................... 568/873, 855

(56) References Cited

U.S. PATENT DOCUMENTS 2,285,329 A * 6/1942 Coleman et al. ............ 260/614
3,383,427 A   5/1968 Wolfe et al.

FOREIGN PATENT DOCUMENTS

| JP | 64-90145 A | | 4/1989 |
| RU | 1816751 | * | 5/1993 |

OTHER PUBLICATIONS

Shavanov et al. Khim. Prom–st., (4), 251–252, 1987; cas-react abstract and Reaction (8) only.*

WPI Derwent English Abstract, abstracting JP 64–90145, Apr. 6, 1989.

Lewis Hatch, et al, "Dehydrohalogenation of Several Vinyl Halides", Dept. of Chemistry, University of Texas, *J. Org. Chem.*, vol. 15, pp. 654–658, Dec. 2, 1949.

Brief Communications, p. 87, abstraacting S. S. Shvanov, et al, "Preparation of Propargyl Alcohol", *Khim. Prom.–st.*, vol. 19, No. 4, pp. 59–60 (1987).

* cited by examiner

*Primary Examiner*—Johann Richter
*Assistant Examiner*—Elvis O. Price
(74) *Attorney, Agent, or Firm*—Sughrue Mion, PLLC

(57) ABSTRACT

Processes are provided for producing propargyl alcohol in an industrially advantageous manner. One of the processes comprises reaction of 1,2,3-trichloropropane with 3 equivalents or more of an alkali compound to produce propargyl alcohol. The other process comprises (1) a first step of reaction of 2,3-dichloro-1-propanol with an amine to produce chloroallyl alcohol, and (2) a second step of reaction of the chloroallyl alcohol obtained in the above step (1) with an alkali compound to produce propargyl alcohol.

24 Claims, No Drawings

US 6,710,213 B2

PRODUCTION PROCESS AND USE FOR PROPARGYL ALCOHOL AND ITS INTERMEDIATE

REFERENCE TO RELATED APPLICATIONS

This application is an application filed under 35 U.S.C. § 111(a) claiming benefit pursuant to 35 U.S.C. § 119(e)(1) of the filing date of Provisional Application 60/230,717 filed Sep. 7, 2000 and Provisional Application 60/216,521 filed Jul. 6, 2000 pursuant to 35 U.S.C. § 111(b).

TECHNICAL FIELD

The present invention relates to a process for producing propargyl alcohol and its intermediate which are useful as a starting material of organic products, and also relates to the use thereof.

RELATED BACKGROUND ART

With respect to the process for producing propargyl alcohol, for example, a method of reacting acetylene with formaldehyde is known and described in JP-A-64-90145 (the term "JP-A" as used herein means an "unexamined published Japanese patent application").

However, this method has a problem in that highly explosive acetylene is used.

In order to solve the problem, a method of producing propargyl alcohol in which chloroallyl alcohol is dehydrochlorinated by reacting with an alkali metal hydroxide is known and described, for example, in U.S. Pat. No. 3,383,427, Khim. Prom-st., 19, 59 (1987), and J. Org. Chem., 15, 654 (1950). With respect to the process for producing chloroallyl alcohol used as a starting material, a method of reacting 1,2,3-trichloropropane with an alkali is known and described, for example, in U.S. Pat. No. 2,285,329.

However, for producing propargyl alcohol, a sufficiently large amount of an amine compound or ammonia must be added in addition to the alkali metal hydroxide. In the case of ammonia, the ammonia is used in an amount as large as 5 to 20 mol per mol of 2-chloroallyl alcohol.

In such a process, the produced propargyl alcohol is liable to decompose or polymerize to lower the productivity, and the isolated and purified propargyl alcohol is also thermally unstable, being liable to decompose or polymerize.

OBJECT OF THE INVENTION

The present invention has been made under these circumstances and the object of the present invention is to provide a process for producing propargyl alcohol ad its intermediate chloroallyl alcohol in an industrially advantageous manner.

DISCLOSURE OF THE INVENTION

As a result of extensive investigations to overcome the above-described problems, the present inventors have found that propargyl alcohol can be produced in a high yield by reacting 1,2,3-trichloropropane with 3 equivalents or more of an alkali compound, and have completed the present invention (first embodiment).

Also, the present inventors have found that a process for producing propargyl alcohol through a step of reacting 2,3-dichloro-1-propanol with an amine to produce chloroallyl alcohol can attain the object, and have completed the present invention (second embodiment).

The present invention provides a production process and a use for propargyl alcohol and its intermediate, described in (1) to (41) below.

(1) A process for producing propargyl alcohol, comprising reacting 1,2,3-trichloropropane with 3 equivalents or more of an alkali compound.
(2) The process for producing propargyl alcohol as described in (1) above, wherein the reaction is performed at a temperature selected from the range of 20° C. to 200° C.
(3) The process for producing propargyl alcohol as described in (1) or (2) above, wherein the reaction is performed under pressure.
(4) The process for producing propargyl alcohol as described in (1) above, wherein the reaction comprises a first step of reacting 1,2,3-trichloropropane with an alkali compound to produce 2-chloroallyl alcohol and a second step of reacting the 2-chloroallyl alcohol with an alkali compound to produce propargyl alcohol.
(5) The process for producing propargyl alcohol as described in (4) above, wherein the first step and the second step are continuously performed.
(6) A process for producing propargyl alcohol, comprising reacting 1,2,3-trichloropropane with an aqueous solution containing 3 equivalents or more of an alkali compound.
(7) The process for producing propargyl alcohol as described in (6) above, wherein the reaction is performed at a temperature selected from the range of 20° C. to 200° C.
(8) The process for producing propargyl alcohol as described in (6) or (7) above, wherein the reaction is performed under pressure.
(9) The process for producing propargyl alcohol as described in (6) above, wherein the reaction comprises a first step of reacting 1,2,3-trichloropropane with an aqueous solution containing an alkali compound to produce 2-chloroallyl alcohol and a second step of reacting the 2-chloroallyl alcohol with an aqueous solution containing an alkali compound to produce propargyl alcohol.
(10) The process for producing propargyl alcohol as described in (9) above, wherein the first step and the second step are continuously performed.
(11) The process for producing propargyl alcohol as described in (1) or (6) above, wherein the alkali compound is at least one compound selected from the group consisting of hydroxides, oxides, carbonates, hydrogencarbonates, phosphates and hydrogenphosphates of an alkali metal and/or an alkaline earth metal.
(12) The process for producing propargyl alcohol as described in (1) or (6) above, wherein the alkali compound is a hydroxide, an oxide and/or a carbonate of an alkali metal and/or an alkaline earth metal.
(13) The process for producing propargyl alcohol as described in (1) or (6) above, wherein the reaction is performed in the presence of a quaternary ammonium salt
(14) A process for producing propargyl alcohol, comprising the following two steps:
 (1) a step of reacting 2,3-dichloro-1-propanol with an amine to produce chloroallyl alcohol, and
 (2) a step of reacting the chloroallyl alcohol obtained in the step (1) with alkali compound to produce propargyl alcohol.
(15) The process for producing propargyl alcohol as described in (14) above, wherein the steps (1) and (2) are continuously performed.
(16) The process for producing propargyl alcohol as described in (14) or (15) above, wherein the step (1) is performed at a temperature of 20 to 300° C. and the step (2) is performed at a temperature of 20 to 200° C.
(17) The process for producing propargyl alcohol as described in (14) or (15) above, wherein the step (1) and/or (2) is performed under pressure.

(18) The process for producing propargyl alcohol as described in (14) or (15) above, wherein the alkali compound in the step (2) is at least one compound selected from the group consisting of hydroxides, oxides, carbonates, hydrogencarbonates, phosphates and hydrogenphosphates of an alkali metal and an alkaline earth metal.
(19) The process for producing propargyl alcohol as described in (1) or (6) or (14) above, wherein the reaction is performed in the presence of a polymerization inhibitor.
(20) The process for producing propargyl alcohol as described in (1) or (6) or (14) above, wherein the process further comprises a purification step performed in the presence of a polymerization inhibitor.
(21) The process for producing propargyl alcohol as described in (19) above, wherein the polymerization inhibitor is at least one compound selected from the group consisting of phenol derivatives, vinyl compounds, sulfur-containing compounds, nitrogen-containing compounds, and metal compounds.
(22) A process for producing chloroallyl alcohol, comprising reacting 2,3-dichloro-1-propanol with an amine.
(23) The process for producing chloroallyl alcohol as described in (22) above, wherein the reaction is performed at a temperature selected from the range of 20° C. to 300° C.
(24) The process for producing chloroallyl alcohol as described in (22) or (23) above, wherein the reaction is performed under pressure.
(25) The process for producing chloroallyl alcohol as described in (22) above, wherein the reaction is performed in the presence of a polymerization inhibitor.
(26) The process for producing chloroallyl alcohol as described in (25) above, wherein the polymerization inhibitor is at least one compound selected from the group consisting of phenol derivatives, vinyl compounds, sulfur-containing compounds, nitrogen-containing compounds, and metal compounds.
(27) Propargyl alcohol, containing a polymerization inhibitor.
(28) The propargyl alcohol as described in (27) above, wherein the polymerization inhibitor is at least one compound selected from the group consisting of phenol derivatives, vinyl compounds, sulfur-containing compounds, nitrogen-containing compounds, and metal compounds.
(29) Propargyl alcohol reduced in formaldehyde, wherein the formaldehyde content is 1,000 ppm or less.
(30) Propargyl alcohol reduced in formaldehyde, wherein the formaldehyde content is 100 ppm or less.
(31) Propargyl alcohol reduced in formaldehyde, wherein the formaldehyde content is 5 ppm or less.
(32) A resin composition, comprising a resin obtained using the propargyl alcohol reduced in formaldehyde as described in any one of (29) to (31) above.
(33) A resin composition, comprising a resin obtained using the propargyl alcohol produced by the production process as described in any one of (1), (6) and (14) above.
(34) The resin composition as described in (32) above, wherein the formaldehyde content is 1,000 ppm or less.
(35) The resin composition as described in (32) above, wherein the formaldehyde content is 100 ppm or less.
(36) The resin composition as described in (32) above, wherein the formaldehyde content is 5 ppm or less.
(37) A resin composition for a cationic electrodeposition coating, comprising a resin obtained using the propargyl alcohol reduced in formaldehyde as described in any one of (29) to (31) above.
(38) A resin composition for a cationic electrodeposition coating, comprising a resin obtained using propargyl alcohol produced by the production process as described in any one of (1), (6) and (14) above.
(39) The resin composition for a cationic electrodeposition coating as described in (37) above, wherein the formaldehyde content is 1,000 ppm or less.
(40) The resin composition for a cationic electrodeposition coating as described in (37) above, wherein the formaldehyde content is 100 ppm or less.
(41) The resin composition for a cationic electrodeposition coating as described in (37) above, wherein the formaldehyde content is 5 ppm or less.

To be brief, the present invention provides "a process for producing propargyl alcohol by reacting 1,2,3-trichloropropane with 3 equivalents or more of an alkali compound", "a process for producing propargyl alcohol, comprising a step of reacting 2,3-dichloro-1-propanol with an amine to produce chloroallyl alcohol and a step of reacting the chloroallyl alcohol obtained in the previous step with an alkali compound to produce propargyl alcohol", "a process for producing chloroallyl alcohol, comprising reacting 2,3-dichloro-1-propanol with an amine", "propargyl alcohol containing a polymerization inhibitor", "propargyl alcohol having a formaldehyde content of 1,000 ppm or less", "a resin composition comprising a resin obtained using propargyl alcohol produced by the above-described process" and "a resin composition for a cationic electrodeposition coating, comprising a resin obtained using propargyl alcohol produced by the above-described process".

BEST MODE FOR CARRYING OUT THE INVENTION

The present invention is described in detail below
[A] The first embodiment of the present invention is described firstly.

The 1,2,3-trichloropropane for use in the present invention is not particularly limited and may be a commercially or industrially available product. Also, 1,2,3-trichloropropane obtained by adding chlorine to an allyl alcohol or an allyl chloride can be used. With respect to the purity, 1,2,3-trichloropropane is preferably purified to a high purity but may contain impurities as long as these impurities have no effect on the reaction and can be removed by the purification process.

The alkali compound for use in the present invention is suitably a compound containing at least one element selected from alkali metals and alkaline earth metals. The alkali metal is selected from Li, Na, K, Rb and Cs, and the alkaline earth metal is selected from Be, Mg, Ca, Sr and Ba. Examples of the compound in which such an element is contained include hydroxides, oxides, carbonates, hydrogencarbonates, phosphates, hydrogenphosphates, oxyhalogenides, basic carbonates, carboxylates and organometal complexes. The alkali metal is preferably Na or K, the alkaline earth metal is preferably Mg or Ca, and the alkali compound is preferably a hydroxide, an oxide, a carbonate, a hydrogencarbonate, a phosphate or a carboxylate thereof. Out of these alkali compounds, one compound may be used alone or two or more may be used in combination at an arbitrary ratio.

In addition, the alkali compound for use in the present invention may be ammonia or an organic base such as amine. Furthermore, a mixture of a compound containing at least one element selected from alkali metals and alkaline earth metals with an organic base may also be used.

The alkali compound is used, in terms of the element selected from alkali metals and alkaline earth metals, in 3 equivalents or more to 1,2,3-trichloropropane. The equivalent is suitably 1 in the case of an alkali metal and it is suitably 2 in the case of an alkaline earth metal. The alkali compound is preferably used in the range from 3 to 20 equivalents, more preferably from 3 to 12 equivalents, still more preferably from 3 to 8 equivalent. If the equivalent ratio of alkali compound/1,2,3-trichloropropane exceeds 20, there arise problems, for example, decomposition of propargyl alcohol occurs due to excess alkali compound or recovery of a large amount of unreacted alkali compound is necessary, whereas if the equivalent ratio of alkali compound/1,2,3-trichloropropane is less than 3, there arise problems, for example, recovery of unreacted intermediate is necessary or the yield decreases.

The production process of the present invention can be performed in the presence of a quaternary ammonium salt. The quaternary ammonium salt is a compound represented by the formula $[R^1R^2R^3R^4N]X$ (wherein $R^1$ to $R^4$ each represents a group selected from an alkyl group or an aryl group, and X represents a monovalent anion), and specific examples thereof include quaternary ammonium salts such as tetraethylammonium chloride, benzyltriethylammonium chloride, tetrabutylammonium chloride, trioctylmethylammonium chloride, trioctylallylammonium chloride, phenyltriethylammonium chloride, tetraethylammonium bromide, triethylcyclohexylammonium bromide, tetrabutylammonium bromide and tetrabutylammonium hydrogensulfate. Out of these compounds, one may be used alone or two or more may be used in combination at an arbitrary ratio.

By adding the quaternary ammonium salt, production of propargyl alcohol can proceed at a high rate and productivity is improved. The molar ratio of the quaternary ammonium salt to the 1,2,3-trichloropropane (quaternary ammonium salt/1,2,3-trichloropropane) is from 0.0001 to 10, preferably from 0.001 to 1.

The process of the present invention can be performed in the presence of a solvent. As the solvent, water, an organic solvent, or the mixtures of water and an organic solvent can be used. Examples of the organic solvent used include hydrocarbon, ether, ketone, amide, nitrite, ester and alcohol, however, the organic solvent is not limited thereto as long as it exerts no effect on the reaction. The solvent is preferably water, and the amount of the water is appropriately selected according to the conditions such as kind, amount of the alkali compound used or reaction temperature. The mass ratio of the organic solvent to 1,2,3-trichloropropane (solvent/1,2,3-trichloropropane) is suitably from 0 to 1,000, preferably from 0 to 100.

The production process of the present invention can be performed in the presence of a polymerization inhibitor. The polymerization inhibitor for use in the present invention includes phenol derivatives, vinyl compounds, sulfur-containing compounds, nitrogen-containing compounds, and metal compounds, but is not limited thereto.

The phenol derivatives include phenol, 4-t-butylphenol, 4-methoxyphenol, 2,5-di-t-butylhydroquinone, 2-t-butyl-4-methylphenol, 2,6-di-t-butylphenol, 2,4,6-trimethylphenol, and 2-i-propyl-5-methyphenol, but are not limited thereto.

The vinyl compounds include styrene, o-chlorostyrene, m-chlorostyrene, p-chlorostyrene, o-bromostyrene, m-bromostyrene, p-bromostyrene, o-nitrostyrene, m-nitrostyrene, p-nitrostyrene, o-cyanostyrene, m-cyanostyrene, p-cyanostyrene, divinylbenzene, p-styrenesonic acid, sodium p-styrenesulfonate, 2-vinylpyridine, 4-vinylpyridine, 2-vinyl-5-ethylpyridine, 2-methyl-5-vinylpyridine, acrylamide, methyl acrylate, and methyl methacrylate, but are not limited thereto.

The sulfur-containing compounds include phenothiazine, 2,2'-dibenzothiazolyl disulfide, 2-mercaptobenzothiazole, sodium salt of 2-mercaptobenzothiazole, and thiourea, but are not limited thereto.

The nitrogen-containing compounds include N-nitrosodiphenylamine, 4-nitrosodiphenylamine, 2-methyl-2-nitrosopropane, α-phenyl(t-butyl)nitrone, N-phenyl-N'-i-propylphenylenediamine, 5,5-dimethyl-N-phenyl-N'-i-propylphenylenediamine, 1-nitroso-2-naphthol, 2-nitroso-1-naphthol, and nitrosobenzene, but are not limited thereto.

The metals of the metal compounds include manganese, zinc, lithium, iron, and copper, but are not limited thereto. The metal compounds include halides, oxyhalides, phosphates, hydrogenphosphates, oxides, hydroxides, carbonates, hydrogencarbonates, basic carbonates, carboxylates, and organometal complexes, but are not limited thereto.

The polymerization inhibitor may be used alone or two or more may be used in combination at an arbitrary ratio.

The added polymerization inhibitor will prevent side reactions such as decomposition and polymerization of propargyl alcohol to improve the productivity, and may reduce formaldehyde formation caused by decomposition, polymerization, or the like of propargyl alcohol.

In the reaction of 1,2,3-trichloropropane with the alkali compound in the present invention, the polymerization inhibitor is used in a molar ratio of polymerization inhibitor/1,2,3-trichloropropane ranging from $1.0 \times 10^{-8}$ to 10.0, preferably from $1.0 \times 10^{-7}$ to 1.0.

In the process of the present invention, the reaction temperature during the production of propargyl alcohol is suitably from 20° C. to 200° C., preferably from 50° C. to 170° C. If the reaction temperature exceeds 200° C., decomposition, polymerization or the like of propargyl alcohol takes place and this is not preferred, whereas if the reaction temperature is less than 20° C., the reaction proceeds at a low rate and the productivity or the like disadvantageously decreases.

The reaction pressure is suitably from 10 kPa to 1,000 kPa, preferably from 50 kPa to 500 kPa. If the reaction pressure is less than 10 kPa or exceeds 1,000 kPa, implementation of the production process is industrially difficult and this is not preferred.

The process of the present invention can also be performed through a first step of reacting 1,2,3-trichloropropane with an alkali compound to produce 2-chloroallyl alcohol and a second step of reacting the 2-chloroallyl alcohol with an alkali compound to produce propargyl alcohol. At this time, the first step and the second step may be performed respectively in the presence of the solvent.

Also, the first step and the second step may be performed continuously, namely in one stage, or may be performed stepwise by varying the conditions as necessary. In each of the first step and the second step, the reaction temperature can be selected from the range of 20° C. to 200° C. and the pressure is from 10 kPa to 1,000 kPa.

The starting materials for use in the present invention each may be introduced into a reactor by any known method and the method is not particularly limited.

For example, a method of previously introducing 1,2,3-trichloropropane and an alkali compound into a reactor and then initiating the reaction or a method of performing the reaction while separately introducing 1,2,3-trichloropropane and an alkali compound may be used. The alkali compound may also be introduced after previously mixing it with 1,2,3-trichloropropane and for example, a method of previously mixing an alkali compound and 1,2,3-trichloropropane by a static mixer (see, *Kagaku Sochi (Chemical Apparatus)*, 74–78 (May, 1994)) and then introducing the mixture into a reactor may be used. In the case of using an organic solvent, a method of introducing 1,2,3-trichloropropane and an alkali compound after diluting them with an organic solvent may be used.

In the production process of the present invention, the reaction may be performed by initially adding 3 equivalents or more of an alkali compound all at once but may also be performed stepwise by adding the alkali compound in parts in the first step where 1,2,3-trichloropropane is reacted with an alkali compound to produce 2-chloroallyl alcohol and in the second step where the 2-chloroallyl alcohol is reacted with an alkali compound to produce propargyl alcohol. The amount of the alkali compound added in each step can be appropriately determined according to the conditions such as reaction temperature.

The quaternary ammonium salt for use in the present invention may be introduced into a reactor by any known method and the method is not particularly limited. For example, a method of previously introducing the quaternary ammonium salt into a reactor and then initiating the reaction or a method of adding the quaternary ammonium salt on demand may be used. Furthermore, as described above, in the case of using water or an organic solvent as a solvent, a method of introducing the quaternary ammonium salt after diluting it with the solvent may be used.

In the present invention, the heat generated upon reaction of 1,2,3-trichloropropane with an alkali compound may be discharged out of the system using water, warm water or heating medium, whereby the reaction temperature can be kept constant. Also, the heat discharged with water, warm water or heating medium may be used as a heat source for other equipment and this is profitable.

As described above, the reaction in the practice of the present invention may be performed by any known method and for example, a batch system, a semibatch system or a continuous system may used. The propargyl alcohol obtained by the present invention can be separated and purified by a known method and for example, a method such as distillation or rectification can be used. The production process of the present invention may include a purification step in the presence of a polymerization inhibitor.

The polymerization inhibitor is used in the purification step in a molar ratio of the polymerization inhibitor to the propargyl alcohol (polymerization inhibitor/propargyl alcohol) ranging from $1.0\times10^{-8}$ to 10.0, preferably from $1.0\times10^{-7}$ to 1.0. The propargyl alcohol may be separated and purified in the presence of the polymerization inhibitor used in the reaction of the 1,2,3-trichloropropane with the alkali compound, or a polymerization inhibitor may be newly added. The newly added polymerization inhibitor may be the same one as in the reaction of the 1,2,3-trichloropropane with the alkali compound, or may be different from that according to the conditions and uses.

The polymerization inhibitor may be added to the propargyl alcohol produced by the above-described process, or the propargyl alcohol purified as described above in the present invention. The polymerization inhibitor is added at a molar ratio of the polymerization inhibitor to the propargyl alcohol (polymerization inhibitor/propargyl alcohol) ranging from $1.0\times10^{-8}$ to 10.0. preferably from $1.0\times10^{-7}$ to 1.0. In the case where the propargyl alcohol after purification retains the polymerization inhibitor added in the purification step, an additional polymerization inhibitor may be added newly or not be added. The newly added polymerization inhibitor may be the same as the one used in the production process or in the purification step, or different from that according to the conditions or the use thereof.

The addition of the polymerization inhibitor we retard side reactions of the propargyl alcohol such as decomposition and polymerization to improve the productivity, and further may reduce the amount of formaldehyde formed by decomposition, polymerization, or the like

[B] The second embodiment of the present invention is described in detail below

The process for producing propargyl alcohol of the present invention is characterized by comprising the following two steps, where the step (1) is a novel reaction:

(1) a step of reacting 2,3-dichloro-1-propanol with an amine to produce chloroallyl alcohol; and (2) a step of reacting the chloroallyl alcohol obtained in the above-described step with an alkali compound to produce propargyl alcohol.

The chloroallyl alcohol obtained in the step (1) of the present invention means 2-chloroallyl alcohol, cis-3-chloroallyl alcohol, trans-3-chloroallyl alcohol or a mixture of two or more thereof.

The 2,3-dichloro-1-propanol for use in the step (1) of the present invention is not particularly limited and may be a commercially or industrially available product. Also, 2,3-dichloro-1-propanol obtained by reacting an allyl alcohol with chlorine or allyl chloride with hypochlorous acid in the production process of epichlorohydrin may be used. With respect to the purity, 2,3-dichloro-1-propanol is preferably purified to a high purity but may contain impurities as long as these impurities have no effect on the reaction and can be removed by the purification process.

The amine for use in the step (1) of the present invention is not particularly limited and may be a commercially or industrially available product. An ammonia or a primary amine, secondary amine or tertiary amine represented by the formula $NR^1R^2R^3$ may be used as the amine. The amine may also contain an imino group and a polyamine having two or more amino groups in the molecule, such as diamine or triamine, may be used. Furthermore, a cyclic amine may also be used.

Specific examples of the monoamine include methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, i-butylamine, di-i-butylamine, tri-i-butylamine, sec-butylamine, di-sec-butylamine, tri-sec-butylamine, tert-butylamine, di-tert-butylamine, tri-tert-butylamine, allylamine diallylamine, triallylamine, cyclohexylamine, dicyclohexylamine, tricyclohexylamine, n-octylamine, di-n-octylamine, tri-n-octylamine, benzylamine, dibenzylamine, tribenzylamine, diaminopropylamine, 2-ethylhexylamine, 3-(2-ethylhexyloxy)propylamine, 3-methoxypropylamine, 3-ethoxypropylamine, 3-(diethylamino)propylamine, bis(2-ethylhexyl)amine, 3-(dibutylamino)propylamine, α-phenylethylamine, β-phenylethylamine, aniline, N-methylaniline, N,N-dimethylaniline, diphenylamine, triphenylamine, o-toluidine, m-toluidine, p-toluidine, o-anisidine, m-anisidine, p-anisidine, o-chloroaniline, m-chloroaniline, p-chloroaniline, o-bromoaniline, m-bromoaniline, p-bromoaniline, o-nitroaniline, m-nitroaniline, p-nitroaniline, 2,4-dinitroaniline, 2,4,6-trinitroaniline, p-aminobenzoic acid, sulfanilic acid, sulfanilamide, monoethanolamine, diethanolamine and triethanolamine.

Examples of the diamine include 1,2-diaminoethane, N,N,N',N'-tetramethyl-1,2-diaminoethane, N,N,N',N'-tetraethyl-1,2-diaminoethane, 1,3-diaminopropane, N,N,N', N'-tetramethyl-1,2-diaminopropane, N,N,N',N'-tetraethyl-1, 2-diaminopropane, 1,4-diaminobutane, N-methyl-1,4-diaminobutane, 1,2-diaminobutane, N,N,N',N'-tetramethyl-1,2-diaminobutane, 3-aminopropyldimethylamine, 1,6-diaminohexane, 3,3-diamino-N-methyldipropylamine, 1,2-phenylenediamine, 1,3-phenylenediamine, 1,4-phenylenediamine and benzidine.

Examples of the triamine include 2,4,6-triaminophenol, 1,2,3-triaminopropane, 1,2,3-triaminobenzene 1,2,4-triaminobenzene and 1,3,5-triaminobenzene. Examples of the tetramine include β,β',β"-triaminotriethylamine.

Specific examples of the cyclic amine include pyrrole, pyridine, pyrimidine, pyrrolidine, piperidine, purine, imidazole, oxazole, thiazole, pyrazole, 3-pyrroline, quinoline, isoquinoline, carbazole, piperazine, pyridazine, 1,2,3-triazine, 1,2,4-triazine, 1,3,5-triazine, 1,2,3-triazole, 1,2,5-triazole, 1,2,4-triazole, 1,3,4-triazole and morpholine. The amine for use in the present invention is by no means limited to the above-described compounds and, for example, an asymmetric compound having different kinds of substituents, such as ethylmethylamine, may also be used. Also, one amine may be used alone or two or more amines may be used in combination at an arbitrary ratio.

Among these, preferred are ammonia, methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, i-butylamine, di-i-butylamine, tri-i-butylamine, sec-butylamine, di-sec-butylamine, tri-sec-butylamine, tert-butylamine, di-tert-butylamine, tri-tert-butylamine, cyclohexylamine, dicyclohexylamine, tricyclohexylamine, benzylamine, dibenzylamine, tribenzylamine, diaminopropylamine, aniline, N-methylanine, N,N-dimethylaniline, diphenylamine, o-toluidine, m-tuldine, p-toluidine, o-anisidine, m-anisidine, p-anisidine, o-chloroaniline, m-chloroaniline, p-chloroaniline, p-aminobenzoic acid, sulfanilic acid, ethylmethylamine, monoethanolamine, diethanolamine, triethanolamine, 1,2-diaminoethane, N,N,N',N'-tetramethyl-1,2-diaminoethane, N,N,N',N'-tetraethyl-1,2-diaminoethane, 1,3-diaminopropane, N,N,N',N'-tetramethyl-1,2-diaminopropane, N,N,N',N'-tetraethyl-1,2-diaminopropane, 1,4-diaminobutane, N-methyl-1,4-diaminobutane, 1,2-diaminobutane, N,N,N',N'-tetramethyl-1,2-diaminobutane, 3-aminopropyldimethylamine, 1,6-diaminohexane, 3,3-diamino-N-methyldipropylamine, 1,2-phenylenediamine, 1,3-phenylenediamine, 1,4-phenylenediamine, benzidine, 2,4,6-triaminophenol, 1,2,3-triaminopropane, 1,2,3-triaminobenzene, 1,2,4-triaminobenzene, 1,3,5-triaminobenzene, β, β', β"-triaminotriethylamine, pyrrole, pyridine, pyrimidine, pyrrolidine, piperidine, purine, imidazole, oxazole, thiazole, pyrazole, 3-pyrroline, quinoline, isoquinoline, carbazole, piperazine, pyridazine, 1,3,5-triazine, 1,2,3-triazole, 1,2,5-triazole and morpholine.

In the step (1) of the process of the present invention, the reaction temperature at the production of chloroallyl alcohol is suitably from 20° C. to 300° C., preferably from 50° C. to 250° C. If the reaction temperature exceeds 300° C., decomposition, polymerization or the like of chloroallyl alcohol takes place, whereas if the reaction temperature is less than 20° C., the reaction proceeds at a low rate and the productivity or the like disadvantageously decreases.

The reaction pressure in the step (1) of the present invention is suitably from 10 kPa to 10,000 kPa, preferably from 50 kPa to 5,000 kPa. If the reaction pressure is less than 10 kPa or exceeds 10,000 kPa, implementation of the production process is industrially difficult and this is not preferred.

The molar ratio between the 2,3-dichloro-1-propanol and the amine (amine/2,3-dichloro-1-propanol) in the step (1) of the present invention is suitably from 0.001 to 1,00, preferably from 0.01 to 100. If the molar ratio of amine/2,3-dichloro-1-propanol exceeds 1,000, there arise problems, for example, recovery of excess unreacted organic base becomes necessary, whereas if the molar ratio of amine/2, 3-dichloro-1-propanol is less than 0.001, there arise problems, for example, recovery of excess 2,3-dichloro-1-propanol becomes necessary. Furthermore, the amine for use in the present invention is preferably used in a stoichiometric amount or more, however, the present invention is not limited thereto.

The step (1) of the present invention can also be performed in the presence of a solvent. Examples of the solvent include water, hydrocarbon, ether, ketone, amide, nitrile, ester and alcohol, however, the solvent is not limited thereto and the above-described amine can also be used as the solvent.

The mass ratio of the solvent to the 2,3-dichloro-1-propanol (solvent/2,3-dichloro-1-propanol) is suitably from 0 to 10,000, preferably from 0 to 1,000, however, the mass ratio is not limited thereto.

The heat generated upon reaction of 2,3-dichloro-1-propanol with an amine may be discharged out of the system using water, warm water or heating medium, whereby the reaction temperature can be kept constant. Also, the heat discharged with water, warm water or heating medium may be used as a heat source for other equipment and this is profitable.

In practicing the step (1) of the present invention, the reaction may be performed by any known method and for example, a batch system, a semibatch system or a continuous system may be used, however, the method is not limited thereto. Also, the starting material for use in the present invention may be introduced into a reactor by any known method and the method is not particularly limited. For example, a method of previously introducing 2,3-dichloro-1-propanol and an amine into a reactor and then initiating the reaction or a method of performing the reaction while introducing 2,3-dichloro-1-propanol and an amine may be used.

In addition, the amine may also be introduced after previously mixing it with 2,3-dichloro-1-propanol and for example, a method of previously mixing an amine and 2,3-dichloro-1-propanol by a static mixer (see, *Kagaku Sochi* (*Chemical Apparatus*), 74–78 (May, 1994)) and then introducing the mixture into a reactor may be used, however, the method is not limited thereto. A method of separately introducing 2,3-dichloro-1-propanol and an amine may also be used. With respect to the 2,3-dichloro-1-propanol, a method of introducing it after the dilution with a solvent may also be used, however, the method is not limited thereto.

The chloroallyl alcohol obtained by the present invention includes 2-chloroallyl alcohol, cis-3-chloroallyl alcohol and trans-3-chloroallyl alcohol. These three kinds of isomers can be separated and purified by a known method and for example, a method such as distillation or rectification can be used. However, in the case of using these three kinds of isomers for the production of propargyl alcohol in the step (2) of the present invention, the mixture of chloroallyl alcohols obtained in the step (1) can be used as the starting material without separating those three kinds of isomers.

The step (2) in the production process of the present invention is described below.

The step (2) is a step for producing propargyl alcohol by reacting chloroallyl alcohol obtained in the above-described step (1) with an alkali compound. The step (2) may be performed by any known method. For example, propargyl alcohol can be produced by reacting chloroallyl alcohol with an alkali compound in the same manner as in U.S. Pat. No. 3,383,427, *Khim. Prom-st.*, 4, 251 (1987), *J. Org. Chem.*, 15, 654 (1950).

The alkali compound for use in the step (2) of the present invention is not particularly limited and may be a commercially or industrially available product. The alkali compound for use in the present invention is suitably a compound containing at least one element selected from alkali metals and alkaline earth metals. Out of these alkali compounds, one compound may be used alone or two or more may be used in combination at an arbitrary ratio.

The alkali compound for use in the step (2) of the present invention may also be an ammonia or an amine. Furthermore, a mixture of a compound containing at least one element selected from alkali metals and alkaline earth metals with an ammonia or an amine may also be used.

In the step (2) of the present invention, the reaction temperature at the production of propargyl alcohol is suitably from 20° C. to 200° C., preferably from 50° C. to 170° C. If the reaction temperature exceeds 200° C. decomposition, polymerization or the like of propargyl alcohol takes place and this is not preferred, whereas if the reaction temperature is less than 20° C., the reaction proceeds at a low rate and the productivity or the like disadvantageously decreases.

The step (2) of the present invention can also be performed in the presence of a solvent. Examples of the solvent include water, hydrocarbon, ether, ketone, amide, nitrile, ester and alcohol, however, the solvent is not limited thereto. In the case of practicing the steps (1) and (2) in the presence of a solvent, a solvent having no effect in either step, if possible, the same solvent, is preferably selected. The mass ratio between the solvent and chloroallyl alcohol (chloroallyl alcohol/solvent) is suitably from 0 to 10,000, preferably from 0 to 1,000, however, the mass ratio is not limited thereto.

The reaction pressure in the step (2) of the present invention is suitably from 10 kPa to 10,000 kPa, preferably from 50 kPa to 5,000 kPa. If the reaction pressure is less than 10 kPa or exceeds 10,000 kPa, implementation of the production process is industrially difficult and this is not preferred.

The molar ratio between the chloroallyl alcohol and the alkali compound (alkali compound/chloroallyl alcohol) for use in the present invention is suitably from 0.001 to 1,000, preferably from 0.01 to 100. If the molar ratio of alkali compound/chloroallyl alcohol exceeds 1,000, there arise problems, for example, recovery of excess unreacted alkali compound becomes necessary, whereas if the molar ratio of alkali compound/chloroallyl alcohol is less than 0.001, there arise problems, for example, recovery of excess chloroallyl alcohol becomes necessary. Furthermore, the alkali compound is preferably used in a stoichiometric amount or more, however, the present invention is not limited thereto.

The heat generated upon reaction of chloroallyl alcohol with an alkali compound may be discharged out of the system using water, warm water or heating medium, whereby the reaction temperature can be kept constant. Also, the heat discharged with water, warm water or heating medium may be used as a heat source for other equipment and this is profitable.

In practicing the step (2) of the present invention, the reaction may be performed by any known method and for example, a batch system, a semibatch system or a continuous system may be used. Also, the starting material may be introduced into a reactor by any known method and the method is not particularly limited. For example, a method of previously introducing chloroallyl alcohol and an alkali compound into a reactor and then initiating the reaction or a method of performing the reaction while continuously introducing chloroallyl alcohol and an alkali compound may be used.

The alkali compound may also be introduced after previously mixing it with chloroallyl alcohol and for example, a method of previously mixing an alkali compound and chloroallyl alcohol by a static mixer (see, *Kagaku Sochi* (*Chemical Apparatus*), 74–78 (May, 1994)) and then introducing the mixture into a reactor may be used, however, the method is not limited thereto.

A method of separately introducing chloroallyl alcohol and an alkali compound may also be used. A method of introducing chloroallyl alcohol after diluting it with a solvent may also be used, however, the method is not limited thereto. In the same manner, a method of introducing an alkali compound after diluting it with a solvent may be used, however, the method is not limited thereto.

The production process of propargyl alcohol of the present invention is described above by referring to the case where the step (1) and the step (2) are performed separately. However, in the present invention, the first step (1) of reacting 2,3-dichloro-1-propanol with an amine to produce chloroallyl alcohol and the second step (2) of reacting the chloroallyl alcohol obtained in the step (1) with an alkali compound to produce propargyl alcohol may also be continuously performed, namely in one stage, and in this case, the reactions may be performed stepwise by varying the conditions.

Both of the above two steps in the production process of the present invention may be performed in the presence of a polymerization inhibitor.

The polymerization inhibitor for use in the present invention includes phenol derivatives, vinyl compounds, sulfur-containing compounds, nitrogen-containing compounds, and metal compounds, but is not limited thereto. The added polymerization inhibitor will prevent side reactions such as decomposition and polymerization of chloroallyl alcohol and propargyl alcohol to improve the productivity, and may reduce the formaldehyde formation caused by decomposition, polymerization, or a like reaction of propargyl alcohol.

In the reaction of the 2,3-dichloro-1-propanol with the amine in the present invention, the polymerization inhibitor is used in a molar ratio of the polymerization inhibitor to the 2,3-dichloro-1-propanol (polymerization inhibitor/2,3-dichloro-1-propanol) ranging from $1.0 \times 10^{-8}$ to 10.0, preferably from $1.0 \times 10^{-7}$ to 1.0. The polymerization inhibitor may be used alone or two or more may be used in combination at an arbitrary ratio.

The step (2) may be performed in the presence of the polymerization inhibitor used in the step (1), or a polymerization inhibitor may be added newly. The newly added polymerization inhibitor may be the same one as in the reaction of the 2,3-dichloro-1-propanol with the amine, or may be different one selected according to the conditions. The polymerization inhibitor is used at a ratio to the chloroallyl alcohol (polymerization inhibitor/chloroallyl alcohol) ranging from $1.0 \times 10^{-8}$ to 10.0, preferably from $1.0 \times 10^{-7}$ to 1.0.

The propargyl alcohol obtained according to the present invention can be separated and purified by a known method and for example, a method such as distillation or rectification can be used. The production process of the present invention may include a purification step in the presence of a polymerization inhibitor. The polymerization inhibitor is used in the purification step at the ratio to the propargyl alcohol (polymerization inhibitor/propargyl alcohol) ranging from $1.0 \times 10^{-8}$ to 10.0, preferably from $1.0 \times 10^{-7}$ to 1.0.

The propargyl alcohol may be separated and purified in the presence of the polymerization inhibitor used in the reaction of the chloroallyl alcohol with the alkali compound, or a polymerization inhibitor may be newly added. The newly added polymerization inhibitor may be the same one as used in the reaction of the chloroallyl alcohol with the alkali compound, or may be different from that according to the conditions and uses thereof.

The added polymerization inhibitor will retard side reactions of propargyl alcohol such as decomposition and polymerization to improve the productivity, and further may reduce the amount of formaldehyde formed by decomposition, polymerization, or a like reaction of the propargyl alcohol.

To the propargyl alcohol obtained through the production process or the purification step of the present invention, a polymerization inhibitor may be added. The polymerization inhibitor is used at the ratio to the propargyl alcohol (polymerization inhibitor/propargyl alcohol) ranging from $1.0 \times 10^{-8}$ to 10.0, preferably from $1.0 \times 10^{-7}$ to 1.0.

If the propargyl alcohol after purification contains the polymerization inhibitor added in the purification step, the polymerization inhibitor need not be added, but may be newly added. The newly added polymerization inhibitor may be the same one as in the production process or the purification step, or may be different from that according to the conditions and uses thereof.

[C] The propargyl alcohol of the present invention (the first embodiment and the second embodiment) is described below.

The propargyl alcohol of the present invention is characterized in that the formaldehyde content is 1,000 ppm or less. The formaldehyde content is preferably 500 ppm or less, more preferably 100 ppm or less, most preferably 5 ppm or less. Formaldehyde has strong chemical affinity and coagulates or denatures proteins of cell protoplasm to adversely affect the human body, for example, the cell is inhibited from all functions and killed. Thus, from the standpoint of environmental issue, propargyl alcohol containing formaldehyde is not preferred and propargyl alcohol reduced in the formaldehyde content is demanded. The propargyl alcohol of the present invention is not started from formaldehyde, therefore, the formaldehyde content thereof can be reduced to 1,000 ppm or less.

[D] The use of the propargyl alcohol obtained according to the present invention (the first embodiment and the second embodiment) is described below.

The propargyl alcohol of the present invention can be used for the application fields, for example, described in JP-A-5-239365. The propargyl alcohol can be used, for example coating resin compositions, and curable resins useful as a molding resin. The compositions and resins are advantageous because of high resistance to humidity, water, saline solutions, solvent, alkali, and acid; high suitability for multiple coating; low curing temperature; and less volume constriction after curing.

Further the propargyl alcohol of the present invention can be used, for example, in a resin containing a triple bond such as ethylyl group or nitrile group within the molecule described in WO98/03701. In this case, the present invention relates to a cationic electrodeposition coating composition containing a resin obtained using the propargyl alcohol produced by the process of the present invention. The cationic electrodeposition coating can apply the coating to fine parts even when the material coated has a complicated shape, therefore, this is being used for general purposes as an undercoating method in the coating of a material having a large size and a complicated shape and required to have high rust preventive property, such as vehicle body. This cationic electrodeposition coating is favored with very high use efficiency of the coating material as compared with other coating methods and in turn ensures high profitability, therefore, is widespread as an industrial coating method.

As described above, the propargyl alcohol of the present invention is characterized in that the formaldehyde content is 1,000 ppm or less, therefore, use thereof is advantageous in view of the effect on human body or the environmental issue.

The resin obtained by the use of the propargyl alcohol of the present invention and the resin composition and the cationic electrodeposition coating composition containing the resin are characterized in that the formaldehyde content is 1,000 ppm or less, therefore, use thereof is advantageous in view of the effect on human body or the environmental issue.

EXAMPLES

The present invention is described in greater detail below by referring to the examples, however, the present invention should not be construed as being limited thereto.

The first embodiment is described by referring to the following Examples.

Example A1

Into an SUS-made 100 ml-volume autoclave, 7.37 g (0.05 mol) of 1,2,3-trichloropropane, 8.48 g (0.08 mol) of $Na_2CO_3$ and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 95% and the yield of propargyl alcohol based on 1,2,3-trichloropropane was 29%.

Example A2

Into an SUS-made 100 ml-volume autoclave, 7.37 g (0.05 mol) of 1,2,3-trichloropropane, 8.48 g (0.08 mol) of $Na_2CO_3$ and 35.0 g of $H_2O$ were charged, and the mixture was reacted in a closed system while thoroughly stirring at a reaction temperature of 170° C. for 4 hours. The reaction solution was quantitated by gas chromatography (FID), as a result, the conversion of 1,2,3-trichloropropane was 100% and the yield of propargyl alcohol based on 1,2,3-trichloropropane was 36%.

Example A3

Into an SUS-made 100 ml-volume autoclave, 7.37 g (0.05 mol) of 1,2,3-trichloropropane, 8.48 g (0.08 mol) of $Na_2CO_3$ and 35.0 g of $H_2O$ were charged, and the mixture was reacted in a closed system while thoroughly stirring at a reaction temperature of 200° C. for 4 hours. The reaction solution was quantitated by gas chromatography (FID), as a result, the conversion of 1,2,3-trichloropropane was 100% and the yield of propargyl alcohol based on 1,2,3-trichloropropane was 39%.

Example A4

Into an SUS-made 100 ml-volume autoclave, 7.37 g (0.05 mol) of 1,2,3-trichloropropane, 10.6 g (0.10 mol) of $Na_2CO_3$ and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 35%.

Example A5

Into an SUS-made 100 ml-volume autoclave, 7.37 g (0.05 mol) of 1,2,3-trichloropropane, 10.6 g (0.10 mol) of $Na_2CO_3$, $5.21 \times 10^{-2}$ g ($5.0 \times 10^{-4}$ mol) of styrene and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 41%.

Example A6

Into an SUS-made 100 ml-volume autoclave, 7.37 g (0.05 mol) of 1,2,3-trichloropropane, 10.6 g (0.10 mol) of $Na_2CO_3$, $5.79 \times 10^{-2}$ g ($5.0 \times 10^{-4}$ mol) of lithium phosphate and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 43%.

Example A7

Into an SUS-made 100 ml-volume autoclave, 7.37 g (0.05 mol) of 1,2,3-trichloropropane, 10.6 g (0.10 mol) of $Na_2CO_3$ $9.91 \times 10^{-2}$ g ($5.0 \times 10^{-4}$ mol) of N-nitrosodiphenylamine and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 42%.

Example A8

Into an SUS-made 100 ml-volume autoclave, 7.37 g (0.05 mol) of 1,2,3-trichloropropane, 5.30 g (0.05 mol) of $Na_2CO_3$, 4.0 g (0.10 mol) of NaOH and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 36%.

Example A9

Into an SUS-made 100 ml-volume autoclave, 7.37 g (0.05 mol) of 1,2,3-trichloropropane, 9.54 g (0.09 mol) of $Na_2CO_3$, 0.80 g (0.02 mol) of NaOH and 35.0 g of $H_2O$ were charged, and the mixture was reacted in a closed system while thoroughly stirring at a reaction temperature of 150° C. for 4 hours. The reaction solution was quantitated by gas chromatography (FID), as a result, the conversion of 1,2,3-trichloropropane was 100% and the yield of propargyl alcohol based on 1,2,3-trichloropropane was 40%.

Example A10

Into an SUS-made 100 ml-volume autoclave, 7.37 g (0.05 mol) of 1,2,3-trichloropropane, 9.54 g (0.09 mol) of $Na_2CO_3$, 0.80 g (0.02 mol) of NaOH and 35.0 g of $H_2O$ were charged, and the mixture was reacted in a closed system while thoroughly stirring at a reaction temperature of 150° C. for 8 hours. The reaction solution was quantitated by gas chromatography (FID), as a result, the conversion of 1,2,3-trichloropropane was 100% and the yield of propargyl alcohol based on 1,2,3-trichloropropane was 44%.

Example A11

Into an SUS-made 100 ml-volume autoclave, 7.37 g (0.05 mol) of 1,2,3-trichloropropane, 10.6 g (0.10 mol) of $Na_2CO_3$, 1.14 g (0.005 mol) of benzyltriethylammonium chloride and 35.0 g of $H_2O$ were charged, and the mixture was reacted while thoroughly stirring at a reaction temperature of 150° C. for 2 hours. The reaction solution was quantitated by gas chromatography (FID), as a result, the conversion of 1,2,3-trichloropropane was 100% and the yield of propargyl alcohol based on 1,2,3-trichloropropane was 35%.

Example A12

Into an SUS-made 100 ml-volume autoclave, 7.37 g (0.05 mol) of 1,2,3-trichloropropane, 10.6 g (0.10 mol) of $Na_2CO_3$, 1.61 g (0.005 mol) of tetra-n-butylammonium bromide and 35.0 g of $H_2O$ were charged, and the mixture was reacted while thoroughly stirring at a reaction temperature of 150° C. for 2 hours. The reaction solution was quantitated by gas chromatography (FID), as a result, the conversion of 1,2,3-trichloropropane was 100% and the yield of propargyl alcohol based on 1,2,3-trichloropropane was 34%.

Example A13

Into an SUS-made 100 ml-volume autoclave, 7.37 g (0.05 mol) of 1,2,3-trichloropropane, 10.6 g (0.10 mol) of $Na_2CO_3$, 0.548 g (0.005 mol) of tetramethylammonium chloride and 35.0 g of $H_2O$ were charged, and the mixture was reacted while thoroughly stirring at a reaction temperature of 150° C. for 2 hours. The reaction solution was quantitated by gas chromatography (FID), as a result, the conversion of 1,2,3-trichloropropane was 100% and the yield of propargyl alcohol based on 1,2,3-trichloropropane was 32%.

Example A14

Into an SUS-made 100 ml-volume autoclave, 7.37 g (0.05 mol) of 1,2,3-trichloropropane, 10.6 g (0.10 mol) of $Na_2CO_3$ and 35.0 g of $H_2O$ were charged, and the mixture was reacted in a closed system while thoroughly stirring at a reaction temperature of 150° C. for 4 hours. After cooling the reaction solution, the pressure was returned to an atmospheric pressure and 4.0 g (0.10 mol) of NaOH was added and further reacted while thoroughly stirring at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 58%.

Example A15

Into an SUS-made 100 ml-volume autoclave, 7.37 g (0.05 mol) of 1,2,3-trichloropropane, 10.6 g (0.10 mol) of $Na_2CO_3$ and 35.0 g of $H_2O$ were charged, and the mixture was reacted in a closed system while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 66%.

Example A16

Into an SUS-made 100 ml-volume autoclave, 7.37 g (0.05 mol) of 1,2,3-trichloropropane, 10.6 g (0.10 mol) of $Na_2CO_3$, $5.21 \times 10^{-2}$ g ($5.0 \times 10^{-4}$ mol) of styrene and 35.0 g of $H_2O$ were charged, and the mixture was reacted in a closed system while thoroughly stirring at a reaction temperature of 150° C. for 4 hours. After cooling the reaction solution, the pressure was retied to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 71%.

Example A17

Into an SUS-made 100 ml-volume autoclave, 7.37 g (0.05 mol) of 1,2,3-trichloropropane, 10.6 g (0.10 mol) of $Na_2CO_3$, $5.79 \times 10^{-2}$ g ($5.0 \times 10^{-4}$ mol) of lithium phosphate and 35.0 g of $H_2O$ were charged, and the mixture was reacted in a closed system while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 70%.

Example A18

Into an SUS-made 100 ml-volume autoclave, 7.37 g (0.05 mol) of 1,2,3-trichloropropane, 10.6 g (0.10 mol) of $Na_2CO_3$, $9.91 \times 10^{-2}$ g ($5.0 \times 10^{-4}$ mol) of N-nitrosodiphenylamine and 35.0 g of $H_2O$ were charged, and the mixture was reacted in a closed system while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 72%.

Example A19

Into an SUS-made 100 ml-volume autoclave, 7.37 g (0.05 mol) of 1,2,3-trichloropropane, 11.1 g (0.15 mol) of $Ca(OH)_2$ and 35.0 g of $H_2O$ were charged, and the mixture was reacted while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 58%.

Example A20

Into an SUS-made 100 ml-volume autoclave, 7.37 g (0.05 mol) of 1,2,3-trichloropropane, 8.41 g (0.15 mol) of CaO and 35.0 g of $H_2O$ were charged, and the mixture was reacted while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 59%.

Example A21

Into an SUS-made 100 ml-volume autoclave, 7.37 g (0.05 mol) of 1,2,3-trichloropropane, 10.0 g (0.10 mol) of $CaCO_3$ and 35.0 g of $H_2O$ were charged, and the mixture was reacted while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 46%.

Example A22

Into an SUS-made 10 ml-volume autoclave, 7.37 g (0.05 mol) of 1,2,3-trichloropropane, 10.6 g (0.10 mol) of $Na_2CO_3$, 114 g (0.005 mol) of benzyltriethylammonium chloride and 35.0 g of $H_2O$ were charged, and the mixture was reacted while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 74%.

Example A23

Into an SUS-made 100 ml-volume autoclave, 7.37 g (0.05 mol) of 1,2,3-trichloropropane, 10.6 g (0.10 mol) of $Na_2CO_3$, 1.14 g (0.005 mol) of benzyltriethylammonium chloride, $5.21\times10^{-2}$ g ($5.0\times10^{-4}$ mol) of styrene and 35.0 g of $H_2O$ were charged, and the mixture was reacted while thoroughly stirring at a reaction temperature of 150° C. for 4 hours. After cooling the reaction solution, the pressure was returned to an atmospheric pressure and 8.0 g (0.10 mol) of an aqueous 50 mass % NaOH solution was added and further reacted at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 76%.

Example A24

Into an SUS-made 100 ml-volume autoclave, 7.37 g (0.05 mol) of 1,2,3-trichloropropane, 10.60 g (0.10 mol) of $Na_2CO_3$ and 35.0 g of $H_2O$ were charged, and the mixture was reacted in a closed system while thoroughly stirring at a reaction temperature of 150° C. for 2 hours. After cooling the reaction solution, the pressure was returned to an atmospheric pressure and 5.61 g (0.10 mol) of KOH was added and reacted while thoroughly stirring at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 78%.

Example A25

Into an SUS-made 100 ml-volume autoclave, 7.37 g (0.05 mol) of 1,2,3-trichloropropane, 10.60 g (0.10 mol) of $Na_2CO_3$, $5.21\times10^{-2}$ g ($5.0\times10^{-4}$ mol) of styrene and 35.0 g of $H_2O$ were charged, and the mixture was reacted in a closed system while thoroughly stirring at a reaction temperature of 150° C. for 2 hours. After cooling the reaction solution, the pressure was returned to an atmospheric pressure and 5.61 g (0.10 mol) of KOH was added and reacted while thoroughly stirring at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 82%.

Example A26

Into an SUS-made 100 ml-volume autoclave, 7.37 g (0.05 mol) of 1,2,3-trichloropropane, 10.60 g (0.10 mol) of $Na_2CO_3$, $5.79\times10^{-2}$ g ($5.0\times10^{-4}$ mol) of lithium phosphate and 35.0 g of $H_2O$ were charged, and the mixture was reacted in a closed system while thoroughly stirring at a reaction temperature of 150° C. for 2 hours. After cooling the reaction solution, the pressure was returned to an atmospheric pressure and 5.61 g (0.10 mol) of KOH was added and reacted while thoroughly stirring at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 81%.

Example A27

Into an SUS-made 100 ml-volume autoclave, 7.37 g (0.05 mol) of 1,2,3-trichloropropane, 10.60 g (0.10 mol) of $Na_2CO_3$, $9.91\times10^{-2}$ g ($5.0\times10^{-4}$ mol) of N-nitrosodiphenylamine and 35.0 g of $H_2$) were charged, and the mixture was reacted in a closed system while thoroughly stirring at a reaction temperature of 150° C. for 2 hours. After cooling the reaction solution, the pressure was returned to an atmospheric pressure and 5.61 g (0.10 mol) of KOH was added and reacted while thoroughly stirring at a reaction temperature of 100° C. for 2 hours. The resulting reaction solution was quantitated by gas chromatography (FID), as a result, the conversion of 1,2,3-trichloropropane was 100% and the yield of propargyl alcohol based on 1,2,3-trichloropropane was 80%.

Example A28

A reaction solution was obtained in a scale 10 times larger than that of Example A15 and neutralized with 35 mass % hydrochloric acid. Thereto, 100 g of diethyl ether was added and after vigorously stirring the resulting mixture, the organic phase was sampled by liquid-liquid separation. The same extracting operation was repeated twice and the organic phases obtained were combined and subjected to distillation under atmospheric pressure. First, diethyl ether as a fraction at the boiling point of 34 to 35° C. was obtained from the top of distillation tower. Subsequently, an azeotropic component comprising water and propargyl alcohol as a fraction at the boiling point of 97 to 98° C. was obtained. The distillation was further continued, then, propargyl alcohol as a fraction at the boiling point of 114 to 115° C. was obtained. The yield of propargyl alcohol was 15.7 g (0.28 mol) and the yield of propargyl alcohol based on 1,2,3-trichloropropane was 56%. From the analysis by gas chromatography (TCD), the formaldehyde content was found to be 80 ppm.

Example 29

The same operation was performed as in Example A28 except that the combined organic phase obtained by the extracting operation was distilled with 0.521 g ($5.0\times10^{-3}$ mol) of styrene added thereto under atmospheric pressure to obtain propargyl alcohol as the fraction at the boiling point of 114 to 115. The yield of propargyl alcohol was 17.7 g (0.32 mol) and the yield of propargyl alcohol based on 1,2,3-trichloropropane was 63%. From the analysis by high-performance liquid chromatography (HPLC), the formaldehyde content was found to be 5 ppm or less which is the lower limit of detection.

Example A30

The same operation was performed as in Example A28 except that the combined organic phase obtained by the extracting operation was distilled with 0.579 g ($5.0\times10^{-3}$ mol) of lithium phosphate added thereto under atmospheric pressure to obtain propargyl alcohol as the fraction at the boiling point of 114 to 115° C. The yield of propargyl alcohol was 17.0 g (0.30 mol) and the yield of propargyl alcohol based on 1,2,3-trichloropropane was 61%. From the analysis by high-performance liquid chromatography (HPLC), the formaldehyde content was found to be 5 ppm or less which is the lower limit of detection.

Example A31

The same operation was performed as in Example A28 except that the combined organic phase obtained by the extracting operation was distilled with 0.991 g ($5.0\times10^{-3}$ mol) of N-nitrosodiphenylamine added thereto under atmospheric pressure to obtain propargyl alcohol as the fraction at the boiling point of 114 to 115° C. The yield of propargyl alcohol was 16.8 g (0.30 mol) and the yield of propargyl alcohol based on 1,2,3-trichloropropane was 60%. From the analysis by high-performance liquid chromatography (HPLC), the formaldehyde content was found to be 5 ppm or less which is the lower limit of detection.

Example A32

A reaction was performed in a scale about 10 times larger than that of Example A16 and then distillation was performed in the same manner as in Example A28, as a result, the yield of propargyl alcohol was 17.4 g (0.31 mol) and the yield of propargyl alcohol based on 1,2,3-trichloropropane was 62%. From the analysis by high-performance liquid chromatography (HPLC), the formaldehyde content was found to be 5 ppm or less which is the lower limit of detection.

Example A33

A reaction was performed in a scale about 10 times larger than that of Example A24 and then distillation was performed in the same manner as in Example A28, as a result, the yield of propargyl alcohol was 18.6 g (0.33 mol) and the yield of propargyl alcohol based on 1,2,3-trichloropropane was 66%. From the analysis by gas chromatography (TCD), the formaldehyde content was found to be 84 ppm.

Example A34

A reaction was performed in a scale about 10 times larger than that of Example A25 and then distillation was performed in the same manner as in Example A28, as a result, the yield of propargyl alcohol was 19.6 g (0.35 mol) and the yield of propargyl alcohol based on 1,2,3-trichloropropane was 70%. From the analysis by high-performance liquid chromatography (HPLC), the formaldehyde content was found to be 5 ppm or less which is the lower limit of detection.

Example A35
Stability Test A1

To 5.61 g (0.10 mol) of propargyl alcohol obtained in the same manner as in Example A32, $1.0 \times 10^{-3}$ g ($1.0 \times 10^{-5}$ mol) of styrene was added. The mixture was heated at 60° C. for 100 days. From the analysis of the resulting propargyl alcohol by high-performance liquid chromatography (HPLC), the formaldehyde content was found to be 5 ppm or less which is the lower limit of detection.

Example A36
Stability Test A2

To 5.61 g (0.10 mol) of propargyl alcohol obtained the same manner as in Example A32, $1.2 \times 10^{-3}$ g ($1.0 \times 10^{-5}$ mol) of lithium phosphate was added. The mixture was heated at 60° C. for 100 days. From the analysis of the resulting propargyl alcohol by high-performance liquid chromatography (HPLC), the formaldehyde content was found to be 5 ppm or less which is the lower knit of detection.

Example A37
Stability Test A3

To 5.61 g (0.10 mol) of propargyl alcohol obtained in the same manner as in Example A32, $2.0 \times 10^{-3}$ g ($1.0 \times 10^{-5}$ mol) of N-nitrosodiphenylamine was added. The mixture was heated at 60° C. for 100 days. From the analysis of the resulting propargyl alcohol by high-performance liquid chromatography (HPLC), the formaldehyde content was found to be 5 ppm or less which is the lower limit of detection.

Next, the second embodiment of the present invention is described by referring to the following Examples.

Example B1

Into an SUS-made 100 ml-volume autoclave, 12.90 g (0.10 mol) of 2,3-dichloro-1-propanol, 10.12 g (0.10 mol) of triethylamine and 20.0 g of diethylene glycol di-n-butyl ether were charged, and the mixture was reacted in a closed system while thoroughly stirring at a reaction temperature of 150° C. for 2 hours. After the completion of reaction, the reaction solution was quantitated by gas chromatography. The yield of chloroallyl alcohol based on 2,3-dichloropropanol and the composition ratio thereof (mol %) are shown in Table 1.

Example B2

A reaction was performed in the same manner as in Example B1 except for using 18.54 g (0.10 mol) of tri-n-butylamine in place of triethylamine. The results are shown in Table 1.

Example B3

A reaction was performed in the same manner as in Example B1 except for using 26.95 g (0.10 mol) of tri-n-hexylamine in place of triethylamine. The results are shown in Table 1.

Example B4

A reaction was performed in the same manner as in Example B1 except for using 28.74 g (0.10 mol) of tribenzylamine in place of triethylamine. The results are shown in Table 1.

Example B5

A reaction was performed in the same manner as in Example B1 except for using 7.31 g (0.10 mol) of diethylamine in place of triethylamine. The results are shown in Table 1.

Example B6

A reaction was performed in the same manner as in Example B1 except for using 12.93 g (0.10 mol) of di-n-butylamine in place of triethylamine. The results are shown in Table 1.

Example B7

A reaction was performed in the same manner as in Example B1 except for using 7.31 g (0.10 mol) of n-butylamine in place of triethylamine. The results are shown in Table 1.

Example B8

A reaction was performed in the same manner as in Example B1 except for using 7.31 g (0.10 mol) of i-butylamine in place of triethylamine. The results are shown in Table 1.

Example B9

A reaction was performed in the same manner as in Example B1 except for using 10.72 g (0.10 mol) of benzylamine in place of triethylamine. The results are shown in Table 1.

Example B10

A reaction was performed in the same manner as in Example B1 except for using 7.91 g (0.10 mol) of pyridine in place of triethylamine. The results are shown in Table 1.

Example B11

A reaction was performed in the same manner as in Example B1 except for using 6.01 g (0.10 mol) of 1,2-diaminoethane in place of triethylamine. The results are shown in Table 1.

Example B12

A reaction was performed in the same manner as in Example B1 except for using 8.82 g (0.10 mol) of 1,4-diaminobutane in place of triethylamine. The results are shown in Table 1.

Example B13

A reaction was performed in the same manner as in Example B1 except for using 11.62 g (0.10 mol) of 1,6-diaminohexane in place of triethylamine. The results are shown in Table 1.

Example B14

A reaction was performed in the same manner as in Example B1 except for using 10.81 g (0.10 mol) of 1,2-phenylenediamine in place of triethylamine. The results are shown in Table 1.

Example B15

A reaction was performed in the same manner as in Example B1 except for using 11.62 g (0.10 mol) of N,N,N',N'-tetramethyl-1,2-diaminoethane in place of triethylamine. The results are shown in Table 1.

Example B16

A reaction was performed in the same manner as in Example B1 except for using 8.61 g (0.10 mol) of piperazine in place of triethylamine. The results are shown in Table 2.

Example B17

A reaction was performed in the same manner as in Example B1 except for using 12.12 g (0.10 mol) of N,N-dimethylaniline in place of triethylamine. The results are shown in Table 2.

Example B18

A reaction was performed in the same manner as in Example B1 except for using 8.01 g (0.10 mol) of pyridazine in place of triethylamine. The results are shown in Table 2.

Example B19

A reaction was performed in the same manner as in Example B1 except for using 6.91 g (0.10 mol) of 1,2,4-triazole in place of triethylamine. The results are shown in Table 2.

Example B20

A reaction was performed in the same manner as in Example B1 except for using 20.0 g of acetonitrile in place of diethylene glycol di-n-butyl ether. The results are shown in Table 2.

Example B21

A reaction was performed in the same manner as in Example B1 except for using 20.0 g of benzonitrile in place of diethylene glycol di-n-butyl ether. The results are shown in Table 2.

Example B22

A reaction was performed in the same manner as in Example B1 except for using 20.0 g of N,N-dimethylformamide in place of diethylene glycol di-n-butyl ether. The results are shown in Table 2.

Example B23

A reaction was performed in the same manner as in Example B1 except for using 20.0 g of 1,2-ethanediol in place of diethylene glycol di-n-butyl ether. The results are shown Table 2.

Example B24

A reaction was performed in the same manner as in Example B1 except for using 20.0 g of 1,2-propanediol in place of diethylene glycol di-n-butyl ether. The results are shown in Table 2.

Example B25

A reaction was performed in the same manner as in Example B1 except for using 20.0 g of 1,4-butanediol in place of diethylene glycol di-n-butyl ether. The results are shown in Table 2.

Example B26

A reaction was performed in the same manner as in Example B1 except for using 20.0 g of dimethylsulfoxide in place of diethylene glycol di-n-butyl ether. The results are shown in Table 2.

Example B27

A reaction was performed in the same manner as in Example B1 except for using 20.0 g of 1,2-dicyanoethane in place of diethylene glycol di-n-butyl ether. The results are shown in Table 2.

Example B28

A reaction was performed in the same manner as in Example B1 except for using 20.0 g of 1,4dicyanoethane in place of diethylene glycol di-n-butyl ether The results are shown in Table 2.

Example B29

A reaction was performed in the same manner as in Example B1 except for using 20.0 g of $H_2O$ in place of diethylene glycol di-n-butyl ether. The results are shown in Table 2.

Example B30

A reaction was performed in the same manner as in Example B1 except for using 40.48 g (0.40 mol) of triethylamine. The results are shown in Table 2.

Example B31

A reaction was performed in the same manner as in Example B1 except for using 5.06 g (0.05 mol) of triethylamine. The results are shown in Table 3.

Example B32

A reaction was performed in the same manner as in Example B1 except for using 40.48 g (0.40 mol) of triethylamine and not using diethylene glycol di-n-butyl ether. The results are shown in Table 3.

Example B33

A reaction was performed in the same manner as in Example B1 except for performing the reaction at a reaction temperature of 100° C. for 2 hours. The results are shown in Table 3.

Example B34

A reaction was performed in the same manner as in Example B1 except for performing the reaction at a reaction temperature of 200° C. for 2 hours. The results are shown in Table 3.

Example B35

A reaction was performed in the same manner as in Example B1 except for performing the reaction at a reaction temperature of 150° C. for 6 hours. The results are shown in Table 3.

Example B36

Into an SUS-made 100 ml-volume autoclave, 12.90 g (0.10 mol) of 2,3-dichloro-1-propanol, 10.12 g (0.10 mol) of triethylamine, 0.104 g (0.0010 mol) of styrene and 20.0 g of acetonitrile were charged, and the mixture was reacted in a closed system while thoroughly stirring at a reaction temperature of 150° C. for 2 hours. The results are shown in Table 3.

Example B37

Into an SUS-made 100 ml-volume autoclave, 12.90 g (0.10 mol) of 2,3-dichloro-1-propanol, 10.12 g (0.10 mol) of triethylamine, 0.116 g (0.0010 mol) of lithium phosphate and 20.0 g of acetonitrile were charged, and the mixture was reacted in a closed system while thoroughly stirring at a reaction temperature of 150° C. for 2 hours. The results are shown in Table 3.

Example B38

Into an SUS-made 100 ml-volume autoclave, 12.90 g (0.10 mol) of 2,3-dichloro-1-propanol, 10.12 g (0.10 mol) of triethylamine, 0.198 g (0.0010 mol) of N-nitrosodiphenylamine and 20.0 g of acetonitrile were charged, and the mixture was reacted in a closed system while thoroughly stirring at a reaction temperature of 150° C. for 2 hours. The results are shown in Table 3.

Example B39

A reaction solution obtained in the scale 10 times larger than that of Example B20 was subjected to distillation under atmospheric pressure. As a result, from the top of distillation tower, acetonitrile was first obtained and then a slight amount of triethylamine was obtained. The distillation was further continued, then, objective chloroallyl alcohol was obtained. The yield of chloroallyl alcohol was 74.2 g (0.80 mol) and the yield of chloroallyl alcohol based on 2,3-dichloro-1-propanol was 80%.

Into a reactor, 74.2 g (0.80 mol) of the thus-obtained chloroallyl alcohol and 640.0 g (1.60 mol) of an aqueous 10 mass % NaOH solution were charged, and the mixture was reacted under atmospheric pressure while thoroughly stirring at a reaction temperature of 100° C. for 4 hours. The reaction solution was quantitated by gas chromatography (FID), as a result, the conversion of chloroallyl alcohol was 100% and the yield of propargyl alcohol based on chloroallyl alcohol was 71%.

Furthermore, the above-described reaction solution was neutralized with 35 mass % hydrochloric acid. Thereto, 100 g of diethyl ether was added and after vigorously stirring the resulting mixture, the organic phase was sampled by liquid-liquid separation. The same extracting operation was repeated twice and the organic phases obtained were combined and subjected to distillation under atmospheric pressure. As a result, from the top of distillation tower, diethyl ether as a fraction at the boiling point of 34 to 35° C. was first obtained. Subsequently, an azeotropic component comprising water and propargyl alcohol as a fraction at the boiling point of 97 to 98° C. was obtained. The distillation was further continued, then, propargyl alcohol as a fraction at the boiling point of 114 to 115° C. was obtained. The yield of propargyl alcohol was 28.6 g (0.51 mol) and the yield of propargyl alcohol based on 2,3-dichloro-1-propanol was 51%. From the analysis of this propargyl alcohol by high-performance liquid chromatography (HPLC), the formaldehyde content was found to be 5 ppm or less which is the lower limit of detection.

Example B40

The same operation was performed as in Example B39 except that the combined organic phase obtained by the extracting operation was distilled with 0.520 g (0.0050 mol) of styrene added thereto under atmospheric pressure to obtain propargyl alcohol as a fraction at the boiling point of 114 to 115° C. The yield of propargyl alcohol was 32.2 g (0.57 mol) and the yield of propargyl alcohol based on the 2,3-dichloro-1-propanol was 57%. From the analysis of this propargyl alcohol by high-performance liquid chromatography (HPLC), the formaldehyde content was found to be 5 ppm or less which is the lower limit of detection.

Example B41

The same operation was performed as in Example B39 except that the combined organic phase obtained by the extracting operation was distilled with 0.579 g (0.0050 mol) of lithium phosphate added thereto under atmospheric pressure to obtain propargyl alcohol as a fraction at the boiling point of 114 to 115° C. The yield of propargyl alcohol was 30.8 g (0.55 mol) and the yield of propargyl alcohol based on the 2,3-dichloro-1-propanol was 55%. From the analysis of this propargyl alcohol by high-performance liquid chromatography (HPLC), the formaldehyde content was found to be 5 ppm or less which is the lower limit of detection.

Example B342

The same operation was performed as in Example B39 except that the combined organic phase obtained by the extracting operation was distilled with 0.991 g (0.0050 mol) of N-nitrosodiphenylamine added thereto under atmospheric pressure to obtain propargyl alcohol as a fraction at the boiling point of 114 to 115° C. The yield of propargyl alcohol was 31.3 g (0.56 mol) and the yield of propargyl alcohol based on the 2,3-dichloro-1-propanol was 56%. From the analysis of this propargyl alcohol by high-performance liquid chromatography (HPLC), the formaldehyde content was found to be 5 ppm or less which is the lower limit of detection.

Example B43

Into a reactor, 9.25 g (0.10 mol) of the chloroallyl alcohol obtained by the distillation in the same manner as in Example B39, 0.104 g (0.0010 mol) of styrene and 80.0 g (0.20 mol) of an aqueous 10 mass % NaOH solution were charged, and the mixture was reacted under atmospheric pressure while thoroughly stirring at a reaction temperature of 100° C. for 4 hours. The reaction solution was quantitated by gas chromatography (FID), as a result, the yield of propargyl alcohol based on chloroallyl alcohol was 83%.

Example B44

Into a reactor, 9.25 g (0.10 mol) of the chloroallyl alcohol obtained by the distillation in the same manner as in Example B39, 0.116 g (0.0010 mol) of lithium phosphate and 80.0 g (0.20 mol) of an aqueous 10 mass % NaOH solution were charged, and the mixture was reacted under atmospheric pressure while thoroughly stirring at a reaction temperature of 100° C. for 4 hours. The reaction solution was quantitated by gas chromatography (FID), as a result, the yield of propargyl alcohol based on chloroallyl alcohol was 82%.

Example B45

Into a reactor, 9.25 g (0.10 mol) of the chloroallyl alcohol obtained by the distillation in the same manner as in Example 139, 0.198 g (0.0010 mol) of N-nitrosodiphenylamine and 80.0 g (0.20 mol) of an aqueous 10 mass % NaOH solution were charged, and the mixture was reacted under atmospheric pressure while thoroughly stirring at a reaction temperature of 100° C. for 4 hours. The reaction solution was quantitated by gas chromatography (FID), as a result, the yield of propargyl alcohol based on chloroallyl alcohol was 81%.

Example B46

Into a reactor, 9.25 g (0.10 mol) of the chloroallyl alcohol obtained by the distillation in the same manner as in Example B39 and 112.2 g (0.20 mol) of an aqueous 10 mass % KOH solution were charged, and the mixture was reacted under atmospheric pressure while thoroughly stirring at a reaction temperature of 100° C. for 4 hours. The reaction solution was quantitated by gas chromatography (FID), as a result, the yield of propargyl alcohol based on chloroallyl alcohol was 80%.

Example B47

A reaction solution obtained in the scale 10 times larger than that of Example B35 was subjected to distillation under atmospheric pressure. As a result, triethylamine was first obtained from the top of distillation tower. The distillation was further continued, then, chloroallyl alcohol was obtained. The yield of chloroallyl alcohol was 73.1 g (0.79 mol) and the yield of chloroallyl alcohol based on 2,3-dichloro-1-propanol was 79%.

Into a reactor, 73.1 g (0.79 mol) of the thus-obtained chloroallyl alcohol and 632 g (1.58 mol) of an aqueous 10 mass % NaOH solution were charged, and the mixture was reacted under atmospheric pressure while thoroughly stirring at a reaction temperature of 100° C. for 4 hours. The reaction solution was quantitated by gas chromatography (FID), as a result, the yield of propargyl alcohol based on chloroallyl alcohol was 72%.

Furthermore, the reaction solution obtained above was neutralized with 35 mass % hydrochloric acid, 100 g of diethyl ether was added thereto, and after vigorously stirring the resulting mixture, the organic phase was sampled by liquid-liquid separation. The same extracting operation was repeated twice and the organic phases obtained were combined and subjected to distillation under atmospheric pressure. As a result, diethyl ether as a fraction at the boiling point of 34 to 35° C. was first obtained from the top of distillation tower. Subsequently, an azeotropic component comprising water and propargyl alcohol as a faction at the boiling point of 97 to 98° C. was obtained. The distillation was further continued, then, propargyl alcohol as a fraction at the boiling point of 114 to 115° C. was obtained. The yield of propargyl alcohol was 29.6 g (0.53 mol) and the yield of propargyl alcohol based on 2,3-dichloro-1-propanol was 53%. From the analysis of this propargyl alcohol by high-performance liquid chromatography (HPLC), the formaldehyde content was found to be 5 ppm or less which is the lower limit of detection.

Example B48

Into an SUS-made autoclave, 12.90 g (0.10 mol) of 2,3-dichloro-1-propanol, 10.12 g (0.10 mol) of triethylamine and 20.0 g of diethylene glycol di-n-butyl ether were charged, and the mixture was reacted in a closed system while thoroughly stirring at a reaction temperature of 150° C. for 6 hours. After cooling the reaction solution, the pressure was returned to atmospheric pressure and 80.0 g (0.20 mol) of an aqueous 10 mass % NaOH solution was added and further reacted at a reaction temperature of 100° C. for 4 hours. The resulting reaction solution was quantitated by gas chromatography (FID), as a result, the conversion of 2,3-dichloro-1-propanol was 100% and the yield of propargyl alcohol based on 2,3-dichloro-1-propanol was 74.8%.

Example B49

Into an SUS-made autoclave, 12.90 g (0.10 mol) of 2,3-dichloro-1-propanol, 10.12 g (0.10 mol) of triethylamine, 0.104 g (0.0010 mol) of styrene and 20.0 g of diethylene glycol di-n-butyl ether were charged, and the mixture was reacted in a closed system while thoroughly stirring at a reaction temperature of 150° C. for 6 hours. After cooling the reaction solution, the pressure was returned to atmospheric pressure and 80.0 g (0.20 mol) of an aqueous 10 mass % NaOH solution was added and further reacted at a reaction temperature of 100° C. for 4 hours. The resulting reaction solution was quantitated by gas chromatography (FID), as a result, the yield of propargyl alcohol based on 2,3-dichloro-1-propanol was 83%.

Example B50

Into an SUS-made autoclave, 12.90 g (0.10 mol) of 2,3-dichloro-1-propanol, 10.12 g (0.10 mol) of triethylamine, 0.116 g (0.0010 mol) of lithium phosphate and 20.0 g of diethylene glycol di-n-butyl ether were charged, and the mixture was reacted in a closed system while thoroughly stirring at a reaction temperature of 150° C. for 6 hours. After cooling the reaction solution, the pressure was returned to atmospheric pressure and 80.0 g (0.20 mol) of an aqueous 10 mass % NaOH solution was added and further reacted at a reaction temperature of 100° C. for 4 hours. The resulting reaction solution was quantitated by gas chromatography (FID), as a result, the yield of propargyl alcohol based on 2,3-dichloro-1-propanol was 81%.

Example B51

Into an SUS-made autoclave, 12.90 g (0.10 mol) of 2,3-dichloro-1-propanol, 10.12 g (0.10 mol) of triethylamine, 0.198 g (0.0010 mol) of N-nitrosodiphenylamine and 20.0 g of diethylene glycol di-n-butyl ether were charged, and the mixture was reacted in a closed system while thoroughly stirring at a reaction temperature of 150° C. for 6 hours. After cooling the reaction solution, the pressure was returned to atmospheric pressure and 80.0 g (0.20 mol) of an aqueous 10 mass % NaOH solution was added and further reacted at a reaction temperature of 100° C. for 4 hours. The resulting reaction solution was quantitated by gas chromatography (FID), as a result, the yield of propargyl alcohol based on 2,3-dichloro-1-propanol was 82%.

Example B52
Stability Test Example B1

To 5.61 g (0.10 mol) of propargyl alcohol obtained in the same manner as in Example B39, 0.0010 g ($1.0 \times 10^{-5}$ mol) of styrene was added. The mixture was heated at 60° C. for 100 days. From the analysis of resulting propargyl alcohol by high-performance liquid chromatography (HPLC), the formaldehyde content was found to be 5 ppm or less which is the lower limit of detection.

Example B53
Stability Test B2

To 5.61 g (0.10 mol) of propargyl alcohol obtained in the same manner as in Example B39, 0.0012 g ($1.0 \times 10^{-5}$ mol) of lithium phosphate was added. The mixture was heated at 60° C. for 100 days. From the analysis of resulting propargyl alcohol by high-performance liquid chromatography (HPLC), the formaldehyde content was found to be 5 ppm or less which is the lower limit of detection.

Example B54
Stability Test B3

To 5.61 g (0.10 mol) of propargyl alcohol obtained in the same manner as in Example B39, 0.0020 g ($1.0 \times 10^{-5}$ mol) of N-nitrosodiphenylamine was added. The mixture was heated at 60° C. for 100 days. From the analysis of resulting propargyl alcohol by high-performance liquid chromatography (HPLC), the formaldehyde content was found to be 5 ppm or less which is the lower limit of detection.

The Effects of the Invention

According to the present invention (the first embodiment), propargyl alcohol can be efficiently produced from 1,2,3-trichloropropane without isolating an intermediate.

Also, according to the present invention (the second embodiment), propargyl alcohol can be efficiently produced from chloroallyl alcohol obtained by reacting 2,3-dichloro-1-propanol with an amine.

TABLE 1

| Example | Amine Solvent | Chloro-allyl alcohol Yield (%) | Composition ratio (mole %) | | |
|---|---|---|---|---|---|
| | | | 2-Chloro-allyl alcohol | 3-cis-Chloro-allyl alcohol | 3-trans-Chloro-allyl alcohol |
| B1 | Triethylamine Diethylene glycol di-n-butyl ether | 60.3 | 81.4 | 9.7 | 8.9 |
| B2 | Tri-n-butylamine Diethylene glycol di-n-butyl ether | 53.2 | 68.7 | 15.7 | 15.7 |
| B3 | Tri-n-hexylamine Diethylene glycol di-n-butyl ether | 48.4 | 71.2 | 13.6 | 15.2 |
| B4 | Tribenzylamine Diethylene glycol di-n-butyl ether | 40.8 | 66.7 | 17.5 | 15.8 |
| B5 | Diethylamine Diethylene glycol di-n-butyl ether | 50.1 | 88.6 | 4.9 | 6.4 |
| B6 | Di-n-butylamine Diethylene glycol di-n-butyl ether | 55.5 | 73.2 | 11.1 | 15.8 |
| B7 | n-Buthylamine Diethylene glycol di-n-butyl ether | 50.0 | 81.5 | 10.0 | 8.5 |
| B8 | i-Butylamine Diethylene glycol di-n-butyl ether | 55.5 | 80.2 | 11.4 | 8.4 |
| B9 | Benzylamine Diethylene glycol di-n-butyl ether | 44.2 | 83.2 | 8.4 | 8.6 |
| B10 | Pyridine Diethylene glycol di-n-butyl ether | 21.0 | 88.2 | 6.2 | 5.6 |
| B11 | 1,2-Diaminoethane Diethylene glycol di-n-butyl ether | 40.2 | 73.5 | 12.8 | 13.7 |
| B12 | 1,4-Diaminobutane Diethylene glycol di-n-butyl ether | 41.1 | 77.5 | 11.2 | 11.3 |
| B13 | 1,6-Diaminohexane Diethylene glycol di-n-butyl ether | 46.9 | 77.4 | 11.3 | 11.3 |
| B14 | 1,2-Phenylenediamine Diethylene glycol di-n-butyl ether | 42.3 | 87.4 | 6.3 | 6.3 |
| B15 | N,N,N',N'-Tetramethylethylenediamine Diethylene glycol di-n-butyl ether | 58.8 | 83.1 | 7.8 | 9.1 |

TABLE 2

| Example | Amine Solvent | Chloro-allyl alcohol Yield (%) | 2-Chloro-allyl alcohol | 3-cis-Chloro-allyl alcohol | 3-trans-Chloro-allyl alcohol |
|---|---|---|---|---|---|
| B16 | Piperazine<br>Diethylene glycol di-n-butyl ether | 53.4 | 78.5 | 11.6 | 9.9 |
| B17 | N,N-Dimethylaniline<br>Diethylene glycol di-n-butyl ether | 30.1 | 85.6 | 7.3 | 7.1 |
| B18 | Pyridazine<br>Diethylene glycol di-n-butyl ether | 28.6 | 88.2 | 6.4 | 5.4 |
| B19 | 1,2,4-Triazole<br>Diethylene glycol di-n-butyl ether | 29.2 | 89.5 | 5.4 | 5.1 |
| B20 | Triethylamine<br>Acetonitrile | 89.8 | 72.6 | 13.8 | 13.7 |
| B21 | Triethylamine<br>Benzonitrile | 71.3 | 76.5 | 12.5 | 11.0 |
| B22 | Triethylamine<br>N,N-Dimethylformamide | 61.4 | 76.2 | 11.9 | 11.8 |
| B23 | Triethylamine<br>1,2-Ethanediol | 76.2 | 89.3 | 5.1 | 5.6 |
| B24 | Triethylamine<br>1,2-Propanediol | 70.5 | 90.2 | 4.8 | 5.0 |
| B25 | Triethylamine<br>1,4-Butanediol | 85.4 | 66.6 | 17.0 | 16.3 |
| B26 | Triethylamine<br>Dimethyl sulfoxide | 42.8 | 78.3 | 10.9 | 10.9 |
| B27 | Triethylamine<br>1,2-Dicyanoethane | 81.8 | 75.2 | 12.7 | 12.1 |
| B28 | Triethylamine<br>1,4-Dicyanobutane | 81.9 | 74.2 | 12.3 | 13.5 |
| B29 | Triethylamine<br>Water | 44.8 | 76.9 | 11.6 | 11.6 |
| B30 | Triethylamine<br>Diethylene glycol di-n-butyl ether | 81.4 | 76.2 | 11.9 | 11.8 |

TABLE 3

| Example | (Polymerization inhibitor)<br>Amine<br>Solvent | Chloro-allyl alcohol Yield (%) | 2-Chloro-allyl alcohol | 3-cis-Chloro-allyl alcohol | 3-trans-Chloro-allyl alcohol |
|---|---|---|---|---|---|
| B31 | Triethylamine<br>Diethylene glycol di-n-butyl ether | 41.5 | 77.0 | 12.0 | 11.0 |
| B32 | Triethylamine<br>— | 24.1 | 99.1 | 0.5 | 0.4 |
| B33 | Triethylamine<br>Diethylene glycol di-n-butyl ether | 90.5 | 82.9 | 9.0 | 8.1 |
| B34 | Triethylamine<br>Diethylene glycol di-n-butyl ether | 41.8 | 81.1 | 9.7 | 9.2 |
| B35 | Triethylamine<br>Diethylene glycol di-n-butyl ether | 88.3 | 81.4 | 9.7 | 8.9 |
| B36 | (Styrene)<br>Triethylamine<br>Acetonitrile | 91.1 | 73.1 | 13.9 | 13.0 |
| B37 | (Lithium phosphate)<br>Triethylamine<br>Acetonitrile | 90.4 | 72.0 | 15.5 | 12.5 |
| B38 | (N-Nitrosodiphenylamine)<br>Triethylamine<br>Acetonitrile | 91.0 | 72.5 | 13.9 | 13.6 |

What is claimed is:

1. A process for producing propargyl alcohol, comprising the following two steps:
   (1) a step of reacting 2,3-dichloro-1-propanol with an amine to produce chloroallyl alcohol, and
   (2) a step of reacting the chloroallyl alcohol obtained in said step (1) with an alkali compound to produce propargyl alcohol.

2. The process for producing propargyl alcohol as claimed in claim 1, wherein said steps (1) and (2) are performed in one stage.

3. The process for producing propargyl alcohol as claimed in claim 1 or 2, wherein said step (1) is performed at a temperature of 20 to 300° C. and said step (2) is performed at a temperature of 20 to 200° C.

4. The process for producing propargyl alcohol as claimed in claim 1 or 2, wherein said step (1) and/or (2) is performed under pressure.

5. The process for producing propargyl alcohol as claimed in claim 1 or 2, wherein the alkali compound in said step (2) is at least one compound selected from the group consisting of hydroxides, oxides, carbonates, hydrogencarbonates, phosphates and hydrogenphosphates of an alkali metal and an alkaline earth metal.

6. A process for producing chloroallyl alcohol, comprising reacting 2,3-dichloro-1-propanol with an amine.

7. The process for producing chloroallyl alcohol as claimed in claim 6, wherein said reaction is performed at a temperature selected from the range of 20° C. to 300° C.

8. The process for producing chloroallyl alcohol as claimed in claim 6 or 7, wherein said reaction is performed under pressure.

9. The process for producing chloroallyl alcohol as claimed in claim 6, wherein the reaction is performed in the presence of a polymerization inhibitor.

10. The process for producing chloroallyl alcohol as claimed in claim 9, wherein the polymerization inhibitor is at least one compound selected from the group consisting of phenol derivatives, vinyl compounds, sulfur-containing compounds, nitrogen-containing compounds, and metal compounds.

11. A process for producing propargyl alcohol, comprising reacting 1,2,3-trichloropropane with 3 equivalents or more of an alkali compound in the presence of a quaternary ammonium salt and/or a polymerization inhibitor; wherein said reaction comprises a first step of reacting 1,2,3-trichloropropane with an alkali compound to produce 2-chloroallyl alcohol and a second step of reacting said 2-chloroallyl alcohol with an alkali compound to produce propargyl alcohol.

12. The process for producing propargyl alcohol as claimed in claim 11, wherein said reaction is performed at a temperature selected from the range of 20° C. to 200° C.

13. The process for producing propargyl alcohol as claimed in claim 11 or 12, wherein said reaction is performed under pressure.

14. The process for producing propargyl alcohol as claimed in claim 11, wherein the first step and the second step are performed in one stage.

15. A process for producing propargyl alcohol, comprising reacting 1,2,3-trichloropropane with an aqueous solution containing 3 equivalents or more of an alkali compound in the presence of a quaternary ammonium salt and/or a polymerization inhibitor; wherein said reaction comprises a first step of reacting 1,2,3-trichloropropane with an aqueous solution containing an alkali compound to produce 2-chloroallyl alcohol and a second step of reacting said 2-chloroallyl alcohol with an aqueous solution containing an alkali compound to produce propargyl alcohol.

16. The process for producing propargyl alcohol as claimed in claim 15, wherein said reaction is performed at a temperature selected from the range of 20° C. to 200° C.

17. The process for producing propargyl alcohol as claimed in claim 15 or 16, wherein said reaction is performed under pressure.

18. The process for producing propargyl alcohol as claimed in claim 15, wherein the first step and the second step are performed in one stage.

19. The process for producing propargyl alcohol as claimed in claim 11 or 15, wherein said alkali compound is at least one compound selected from the group consisting of hydroxides, oxides, carbonates, hydrogencarbonates, phosphates and hydrogenphosphates of an alkali metal and/or an alkaline earth metal.

20. The process for producing propargyl alcohol as claimed in claim 11 or 15, wherein said alkali compound is a hydroxide, an oxide and/or a carbonate of an alkali metal and/or an alkaline earth metal.

21. The process for producing propargyl alcohol as claimed in claim 1, wherein the reaction is performed in the presence of a polymerization inhibitor.

22. The process for producing propargyl alcohol as claimed in any one of claims 11, 15 and 1, wherein the process further comprises a purification step performed in the presence of a polymerization inhibitor.

23. The process for producing propargyl alcohol as claimed in claim 11 or 15, wherein the polymerization inhibitor is at least one compound selected from the group consisting of phenol derivatives, vinyl compounds, sulfur-containing compounds, nitrogen-containing compounds, and metal compounds.

24. The process for producing propargyl alcohol as claimed in claim 21, wherein the polymerization inhibitor is at least one compound selected from the group consisting of phenol derivatives, vinyl compounds, sulfur-containing compounds, nitrogen-containing compounds, and metal compounds.

* * * * *